United States Patent [19]
Willenborg et al.

[11] Patent Number: 5,837,709
[45] Date of Patent: Nov. 17, 1998

[54] USE OF CASTANOSPERMINE AS AN ANTI-INFLAMMATORY AND IMMUNOSUPRESSANT AGENT

[75] Inventors: David Otto Willenborg, Sterling; William Butler Cowden, Crozier Circuit Kambah; Christopher Richard Parish, Campbell, all of Australia

[73] Assignee: The Australian National University, Acton, Australia

[21] Appl. No.: 482,083

[22] Filed: Jun. 7, 1995

Related U.S. Application Data

[63] Continuation-in-part of Ser. No. 38,050, Mar. 29, 1993, which is a continuation of Ser. No. 656,073, Mar. 6, 1991, abandoned.

[30] Foreign Application Priority Data

Aug. 10, 1988 [AU] Australia .............................. PI 9759/88

[51] Int. Cl.$^6$ ..................................................... A61K 31/44
[52] U.S. Cl. .............................................................. 514/299
[58] Field of Search ................................................ 514/299

*Primary Examiner*—Jerome D. Goldberg
*Attorney, Agent, or Firm*—Bacon & Thomas

[57] ABSTRACT

A method of anti-inflammatory and/or immunosuppressive treatment of a human or otheer warm-blooded animal patient comprises administration to the patient of an effective amount of castanospermine.

14 Claims, 7 Drawing Sheets

USE OF CASTANOSPERMINE AS AN ANTI-INFLAMMATORY AND IMMUNOSUPRESSANT AGENT

This application is a Continuation-in-Part of application Ser. No. 08/038,050, filed Mar. 29, 1993; which is a Continuation of application Ser. No. 07/656,073, filed Mar. 6, 1991, now abandoned.

This invention relates to the use of castanospermine, an alkaloid of the indolizidine class extracted from an Australian native legume, as an anti-inflammatory and immunosuppressant agent.

Castanospermine (CS) is a recently described alkaloid of the indolizidine class, first isolated from the seeds of the Australian legume, Castanospermum australe (Hohenschutz et al, 1981), and has the structural formula:

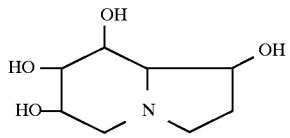

CS is a potent inhibitor of glucosidase I, which has been shown to inhibit oligosaccharide processing in vitro (Sasak et al., 1985, Humphries et al., 1986 and Gross et al., 1986). The alkaloid also inhibits the enzymes β-glucosidase and β-glucocerebrosidase in vitro (Saul et al, 1983) and α-glucosidase both in vivo (Saul et al, 1985) and in vitro (Saul et al., 1983; Ellmers et al., 1987 and Chambers and Elbein, 1986).

International Patent Specification WO 8703903, describes the use of glucosidase I inhibitors, preferably castanospermine, as therapeutic agents for combating non-defective retroviral pathogens, including the aetiological agents of AIDS and feline leukaemia. In this specification, the action of the glucosidase I inhibitor is described as interrupting the replication of the retrovirus in infected cells, alleviating pathogenic effects associated with the presentation of viral env glycoproteins on infected cells, and possibly also preventing infection of target cells by interrupting expression of endogenous receptors recognised by the virion.

In addition, European Patent Specification No. 202661 describes the use of a castanospermine-containing composition for the treatment of diabetes, preferably treating postprandial hyperglycaemia or inhibiting carbohydrate absorption in diabetics. In this specification, the activity of castanospermine is described as inhibition of digestive enzymes, thereby reducing the formation of glucose by hydrolysis of complex sugars, as well as inhibition of increased lipid biosynthesis, thereby preventing hyperlipidemia and excessive accumulation of lipids.

In work leading to the present invention, castanospermine has been found to have an inhibitory effect on passively induced EAE (experimental autoimmune encephalomyelitis, also known as experimental allergic encephalomyelitis) when given to recipient animals.

Experimental autoimmune encephalomyelitis is a cell-mediated autoimmune, demyelinating disease of the central nervous system (CNS) (Paterson, 1976; Bernard, et al., 1983). It can be readily induced in a number of animal species by injection of basic protein of myelin (BP) incorporated in complete Freund's adjuvant (CFA). It can also be induced passively by injecting lymphoid cells from CNS antigen sensitized donors into naive syngenetic recipients (Paterson, 1960; Stone, 1961; Levine and Sowinski, 1967).

Because of the demyelinating character of EAE it has been used extensively as a model of the human demyelinating disease multiple sclerosis (MS). As a consequence much effort has been directed towards finding ways of inhibiting or suppressing the disease. To this end the most logically relevant studies would be those examining ways to inhibit the effector phase of the disease, i.e. the neuroimmunologic inflammation. Lymphocyte-macrophage interactions are thought to be very important in this inflammatory response. Sensitized lymphocytes, upon entering the CNS, probably recognise specific antigen, i.e. BP, which triggers them to release soluble mediators. These mediators then attract and activate macrophages, which are thought to be the ultimate mediators of demyelination. Inhibition of this process could occur at a number of levels, e.g. blocking lymphocyte-endothelial cell interaction, thereby, preventing entrance of cells into the CNS; inhibition of mediator production/action or inhibition of the activity of the activated macrophages.

Recently, it has been demonstrated that sulphated polysaccharides, such as heparin and fucoidin are powerful inhibitors of the CNS inflammation of EAE (Willenborg and Parish, 1988). This inhibition was not due solely to the anticoagulant activity of these compounds since a heparin preparation devoid of anticoagulant activity also partly inhibited the disease. The precise mechanism of inhibition with these agents is not known but these studies strongly implicate carbohydrate residues in some critical step of the inflammatory process.

Castanospermine has also been found to exhibit an anti-inflammatory effect on passively induced adjuvant arthritis, as well as in actively induced arthritis. Adjuvant-induced arthritis in the rat shares a number of features with arthritis in humans, viz. the presence of a proliferative synovitis and subcutaneous nodules, swelling of extremities, and ultimately cartilage and bone erosion. This animal model has been extensively used for detection of anti-inflammatory and immunosuppressive drugs.

Finally, castanospermine has been found to be effective as an immunosuppressant in preliminary experiments, particularly in preventing tissue graft rejection, and in controlling the delayed hypersensitivity reaction.

In a first aspect, therefore, the present invention relates to the use of castanospermine as an anti-inflammatory and/or immunosuppressive agent. In this aspect, this invention provides a method of anti-inflammatory and/or immunosuppressive treatment of a human or other warm-blooded animal patient in need of such treatment, which comprises administration to the patient of an effective amount of castanospermine.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral or parenteral (e.g. subcutaneous, intramuscular and intravenous) routes.

The compositions may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a solution or suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. In addition, sterile, fixed oils are conventionally employed as a solvent or suspending medium.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, pump-based hardware delivery systems can be used, some of which are adapted for implantation.

Oral administration for many conditions will be preferred because of the convenience to the patient, although parenteral and localised sustained release delivery may be even more desirable for certain treatment regimens.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

The effective amount of castanospermine may, for example, comprise from 0.01 to 500 mg/kg/day, preferably from 10 to 500 mg/kg/day.

In another aspect, this invention relates to the use of castanospermine in the preparation or manufacture of a pharmaceutical or veterinary composition for anti-inflammatory and/or immunosuppressive treatment. In this aspect, there is provided a pharmaceutical or veterinary composition which comprises castanospermine, together with an acceptable pharmaceutical or veterinary carrier or diluent therefor.

The formulation of such therapeutic compositions is well known to persons skilled in this field. Suitable pharmaceutically and veterinarily acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically and veterinarily active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical and veterinary compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the subjects to be treated; each unit containing a predetermined quantity of active ingredient calculated to produce the desired therapeutic effect in association with the required pharmaceutical or veterinary carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

The anti-inflammatory and immunosuppressive effects of castanospermine, and administration by both the parenteral and oral routes, are further demonstrated in the following Examples.

EXAMPLE 1

Figure 1A:
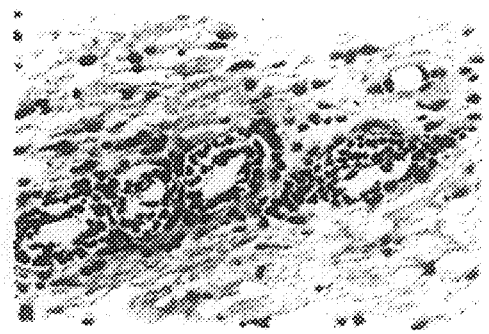
FIGS. 1a–1f, FIGS. 2a–2f, FIG. 3 and FIG. 4 are histological photomicrographs of rat tissue samples.

Inhibition of EAE by Castanospermine a. Materials and Methods

Animals.

Female Lewis (RT-1') rats weighing 150 to 200 g were obtained from the Animal Breeding Establishment of the John Curtin School of Medical Research.

Induction of EAE.

Guinea pig BP was prepared according to the method of Deibler et al, (1972) and BP in saline was emulsified in an equal volume of incomplete Freund's adjuvant containing 4 mg/ml added *Mycobacterium butyricum*. Rats received 0.1 ml of emulsion in one footpad of both hind feet. Total dose received was 50 $\mu$g of BP and 400 $\mu$g of *Mycobacterium butyricum*.

Passive EAE.

Cells for passive transfer of EAE were generated following the method of Painitch and McFarlin (1977). Single cell suspensions were prepared from spleens of donor rats sensitized 10–12 days previously with BP-CFA as described above. Cells were cultured at $2 \times 10^6$/ml in RPMI with 5% fetal calf serum (FCS), $5 \times 10^{-5}$M 2-mercaptoethanol, 200 mM L-glutamine and penicillin and streptomycin. Concanavalin A was added at 2 mg/ml and cultures were incubated at 37° in an atmosphere of 10% $CO_2$, 7% $O_2$ and the balance $N_2$. Cells were harvested after 72 hrs, washed with Hank's balanced salt solution (HBSS) and transferred to recipient animals via a lateral tail vein. All transfer populations contained $30 \times 10^6$ viable cells.

Evaluation of Clinical EAE.

Clinical EAE was graded according to the following scheme: 0—asymptomatic; 1—flaccid distal half of tail; 2—entire tail flaccid; 3—ataxia, difficulty with righting; 4—hindlimb weakness; 5—hindlimb paralysis.

Castanospermine (CS).

Castanospermine was prepared by the method of Hohenschutz et al., 1981. Because of the anticipated short half-life of CS it was administered in mini-osmotic pumps (Alza model 2ML1) which deliver 10 µl/hr over 7 days. The pumps were implanted subcutaneously in the back of rats and in each experiment control rats were sham operated.

b. Results.

Preliminary toxicity studies (data not shown) indicated that CS given at 500 mg/kg/day for 7 days had no apparent toxic effect on animals observed for a 6 week period after treatment. In the first experiment the effect of 100, 200 or 300 mg/kg/day of CS on passively induced EAE was examined. In this experiment the osmotic pumps containing CS were implanted at the time of cell transfer. Table 1 shows that 300 mg/kg/day gave complete protection against clinical EAE, whereas 200 mg/kg/day afforded only partial protection as seen by a decrease in the mean clinical score. 100 mg/kg/day had no protective effect.

Figure 1B:
Figure 1C:
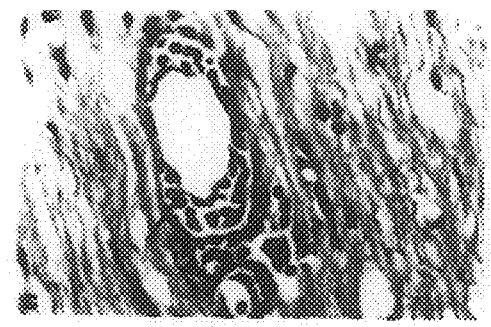
Figure 1D:
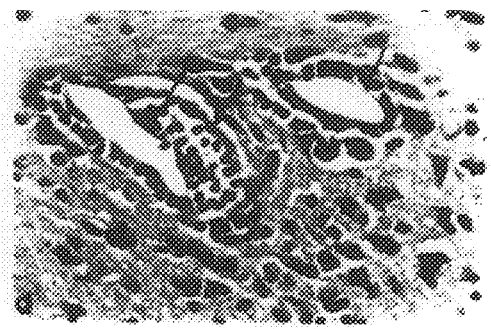
Figure 1E:
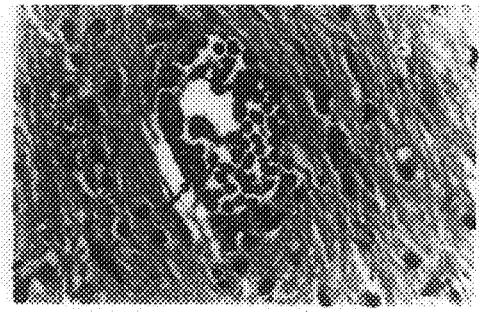
Figure 1F:
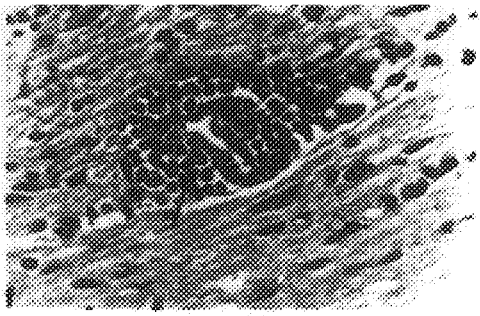
Figure 2A:
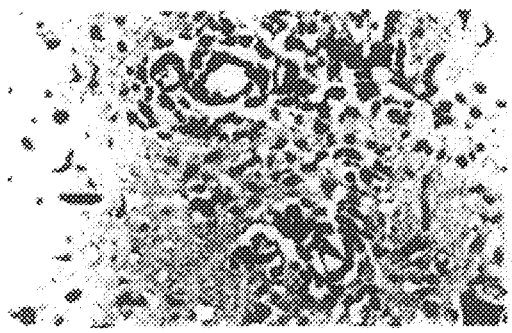
Figure 2B:
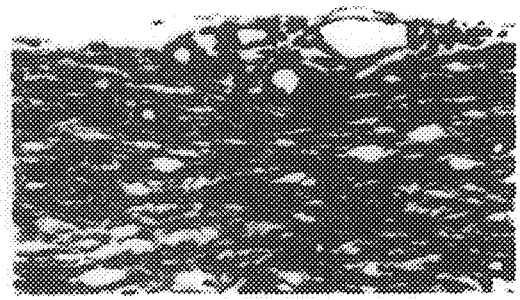
Figure 2C:
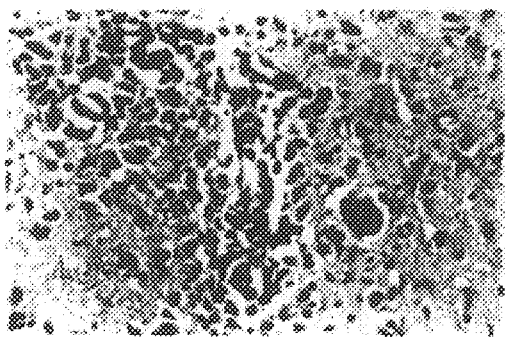
Figure 2D:
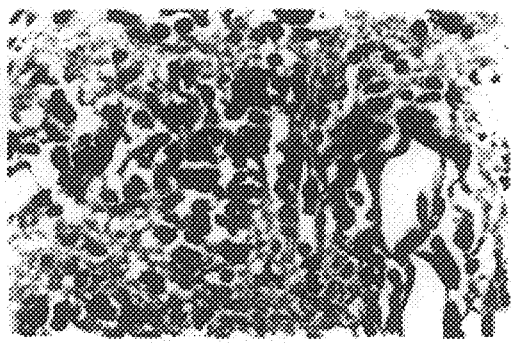
Figure 2E:
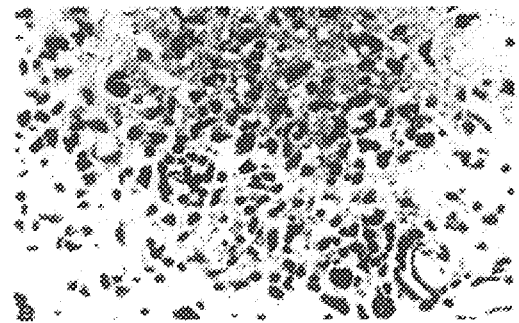
Figure 2F:
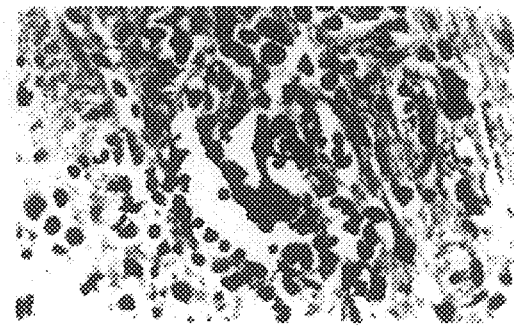

Control rats and those receiving 300 mg/kg/day of CS were killed at day 8 for histological examination of CNS tissues. FIGS. 1a–1f and FIGS. 2a–2f are photomicrographs taken for histological examination, respectively, of a rat treated with CS (300 mg/kg/day) from time of cell transfer to day 7, and a control (untreated) rat. In FIGS. 1a–1f, though no clinical EAE was seen numerous inflammatory lesions were present in the lower spinal cord; FIG. 1a and FIGS. 1c–1f show intense, compact perivascular inflammatory lesions. Solid arrows point to endothelium and show that cells have migrated through the endothelium. Broken arrows show some structure possibly responsible for limiting further cell migration into the parenchyma. FIG. 1b shows intense meningitis in treated rat. FIGS. 2a and 2c–2f show diffuse inflammatory lesions. FIG. 2b shows mild meningeal involvement. Treated rats, surprisingly, had approximately the same number of inflammatory lesions as untreated rats, however, the distribution and quality of lesions was different.

Figure 3:
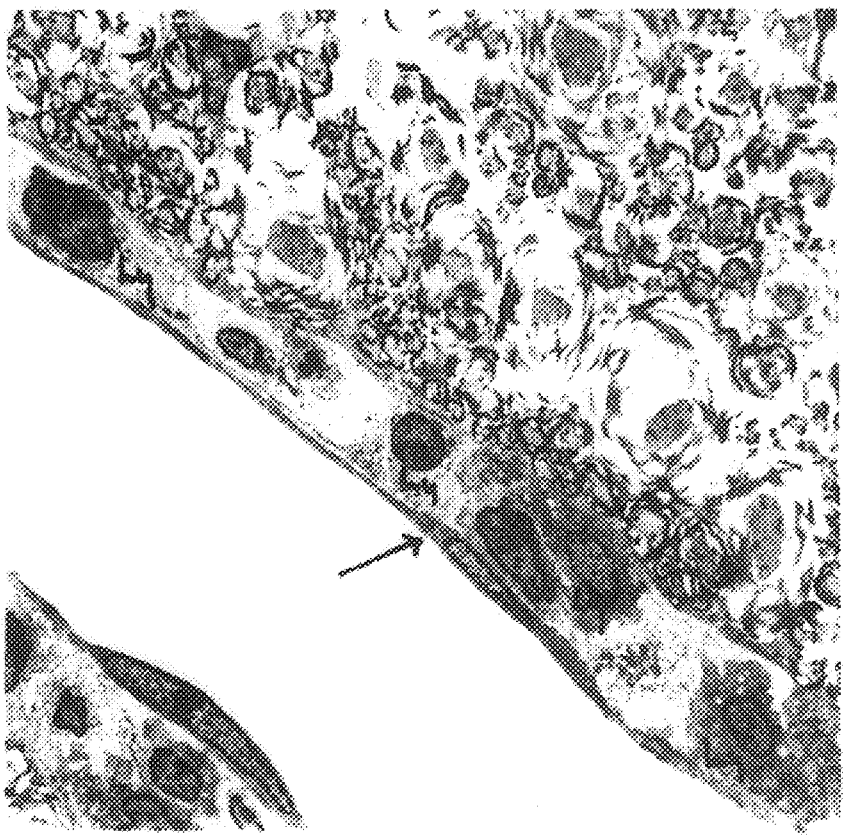
Figure 4:
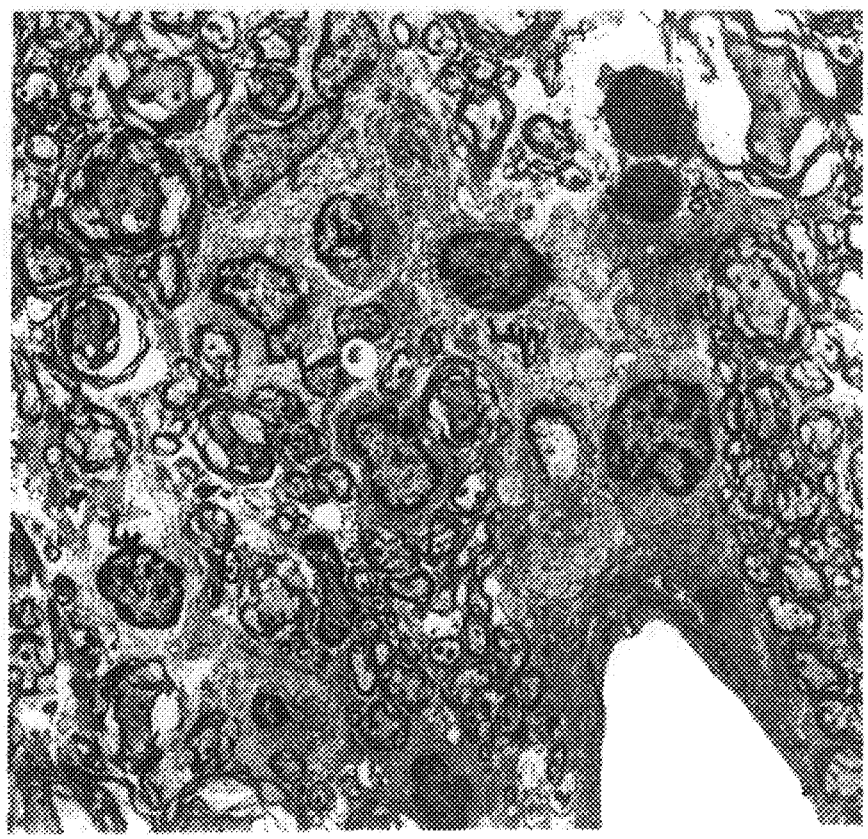

Treated rats showed intense inflammatory infiltrates in the meninges of the spinal cord as well as frequent involvement of the root exit and entrance zones. Meningeal involvement in control animals was seen only rarely and when seen was mild. Furthermore, perivascular inflammatory lesions in CS treated rats were often very intense but were compact with inflammatory cells remaining closely marginated around the vessels. In contrast, lesions in control rats were more diffuse with cells migrating away from the vessels and infiltrating extensively into the parenchyma of the spinal cord. The photomicrographs of FIG. 3 shows that in rats which received CS 300 mg/kg/day via osmotic pump beginning at time of EAE cell transfer (no clinical disease observed and animal killed on day 8 for electron microscopy), lymphoid cells (Ly) have crossed the venular endothelium (arrow) but have failed to enter the parenchyma of the brain. In contrast, FIG. 4 shows that in an untreated control rat showing clinical EAE on day 8 after EAE cell transfer, there has been infiltration of lymphoid cells (Ly) into brain parenchyma.

The ability of CS to inhibit passively induced EAE in recipient animals which had an already compromised blood-brain barrier, brought about by a previous episode of passively induced disease, was examined. Rats recovered from one episode of passively induced disease are equally as susceptible to a second challenge as are naive animals (Willenborg 1979; Hinrichs et al, 1981). When such animals were implanted with a pump delivering CS at 300 mg/kg/day on the day of secondary transfer they did not develop a second episode of the disease (Table 2). The same dose of CS (300 mg/kg) was again shown to protect naive animals from primary disease.

The ability of CS to inhibit disease when treatment was delayed for some days after transfer of the cells was also examined. Two 150 mg/kg injections of CS were given intraperitoneally morning and evening, beginning 4 days after cell transfer and continuing for 3 days. As shown in Table 3 (exp.1) these animals did not develop clinical signs of EAE. When this experiment was repeated, however, treated animals were not protected; all developed clinical disease (exp.2; Table 3). Examination of the data showed, however, that in the first experiment disease signs in untreated animals were not apparent until day 6, whereas, in the second experiment all animals had at least minimal signs at the time treatment was begun. It would appear, therefore, that suppression by CS is most effective if treatment is started before onset of disease symptoms. Another explanation for these findings is that twice daily injections in the second experiment somehow failed to maintain adequate drug levels. To examine this possibility, an experiment was performed in which osmotic pumps were implanted on day 4 after cell transfer. In this experiment all animals showed mild clinical signs on day 4 and treatment with CS failed to modify subsequent disease expression (exp.3; Table 3), suggesting that treatment must be initiated before onset of clinical signs.

The above results show that the alkaloid castanospermine inhibits passively induced experimental autoimmune encephalomyelitis in a dose-dependent manner when the drug is given before onset of clinical disease. Histology taken from treated animals provides some insight into the potential mechanism by which CS inhibits EAE. Contrary to what might have been expected from the clinical picture, lesions were found in treated animals. These were characteristically intense but compact, with inflammatory cells tightly packed around the vessels and little migration into the parenchyma in comparison with controls. The cells were clearly able to cross the endothelium but subsequently appeared to accumulate between the endothelium and some presumably limiting structure. The presence of these lesions suggests that CS does riot work by inhibiting emigration of lymphocytes from blood across the endothelium but may function by blocking the further penetration of effector cells into the parenchyma of the CNS.

The mechanisms responsible for this activity are not known but based upon previous findings with heparin in passively-induced EAE (Willenborg and Parish, 1988), it is conceivable that CS may be working by inhibiting enzymatic activity needed for effector cell emigration across the vascular endothelium and its underlying basal lamina. CS is known to inhibit specific steps in N-linked oligosaccharide processing necessary for the formation of so-called high mannose structures, which, after phosphorylation, become specific recognition markers of lysosomal enzymes. In the absence of these markers lysosomal enzymes cannot be transported from the rough endoplasmic reticulum/Golgi complex to the lysosomes nor can they be recaptured on the cell surface and internalized as they normally would (von Figura and Hasilik, 1986; West, 1986; Kornfield, 1987). Thus, the overall effect of CS might be to cause depletion or at least functional depletion of enzymes necessary for emigration of EAE effector cells from the venules into the parenchyma of the brain. The ultimate inability of the inflammatory cells to penetrate the parenchyma prevents clinical disease. There are, of course, other possible mechanisms by which CS may be functioning such as the inappropriate glycosylation of cell surface proteins—a process to which the anti-metastatic activity of CS has been attributed (Humphries et al., 1986).

TABLE 1

Protective effects of CS on passive EAE.

| CS dose[a] mg/kg/day | Animals with EAE | Mean day of onset | mean[b] clinical score |
|---|---|---|---|
| none | 4/4 | 4 ± 0 | 4.25 ± 0.14 |
| 100 | 4/4 | 4 ± 0 | 4.0 ± 0 |
| 200 | 4/4 | 5 ± 0 | 2.0 ± 0 |
| 300 | 0/4 | — | 0 |

[a]Drug was delivered in miniosmotic pumps placed subcutaneously at the time of cell transfer.
[b]Mean score out of possible 5 ± standard errors.

TABLE 2

Effect of CS on passive EAE in rats with a compromised blood-brain barrier.

| Rats | CS dose[a] mg/kg/day | Animals with EAE | mean[b] clinical score |
|---|---|---|---|
| naive | 0 | 4/4 | 3.75 ± 0.14 |
| naive | 300 | 0/4 | 0 |
| convalescent | 0 | 4/4 | 4 ± 0 |
| convalescent | 300 | 0/4 | 0 |

[a]Drug was delivered in miniosmotic pumps placed subcutaneously at the time of cell transfer.
[b]Mean score out of possible 5 ± standard errors.

TABLE 3

Failure of CS to modulate EAE when given after onset of clinical signs.

| Experiment Number | Treatment[a] | Animals with EAE | mean[b] clinical score |
|---|---|---|---|
| 1 | saline | 4/4 | 3.5 ± 0.28 |
|   | CS 150 mg/kg i.p., 12 hourly | 0/3 | 0 |
| 2 | saline | 4/4 | 4 ± 0.2 |
|   | CS 150 mg/kg i.p., 12 hourly | 3/3 | 4 ± 0 |
| 3 | saline | 4/4 | 4 ± 0 |
|   | CS 300 mg/kg osmotic pump | 5/5 | 4 ± 0 |

[a]Treatment initiated on day 4.
[b]Mean score out of possible 5 ± standard errors.

EXAMPLE 2

Example 1 demonstrates the inhibition of EAE by parenterally administered castanospermine (CS). Other experiments have shown that CS is effective in preventing EAE when the drug is administered orally in the drinking water beginning two or three days before cell transfer; the results of a typical experiment are shown in Table 4. Even when disease symptoms occurred in the treated animals they were invariably mild. It was not possible to treat animals with higher doses of CS by this route since they refused to consume water containing higher concentrations of drug.

TABLE 4

Protective effect of orally administered CS on passively-transferred EAE.

| CS dose[a] mg/kg/day | Animals with EAE | Mean day of onset | Mean[b] clinical score |
|---|---|---|---|
| none | 5/5 | 5 (±0) | 2.75 (±0.25) |
| 80 | 0/4 | — | 0 |

[a]Drug was delivered in drinking water (1.35 g/litre) beginning 3 days before cell transfer; food and water consumption was similar for treated and control groups.
[b]Mean score out of possible 5 ± standard errors.

EXAMPLE 3

Effect of Castanospermine on Passively Induced Adjuvant Arthritis a. Methods (DAxLewis)F$_1$ rats were immunized with 3 mg M. butyricum in light mineral oil injected intradermally in both hind feet. Ten days later spleens were removed and made into a single cell suspension in RPMI containing 5% fetal calf serum, 200 mM L Glutamine, $5 \times 10^{-5}$M 2-ME, penicillin and streptomycin. Cells were adjusted to $2 \times 10^6$ cells/ml, and cultured in 50 ml media in 75 mm culture flasks. ConA was added at 2 mg/ml and cultures incubated for 72 hrs at 37° C. in an atmosphere of 10% $CO_2$, 7% $O_2$ and the balance $N_2$. Cells were then washed and transferred at $50 \times 10^6$ or $60 \times 10^6$ cells/rat i.v. into 10 weeks old male (DAxLewis)F$_1$.

Castanospermine was put in osmotic pumps (Alza Corp.) which delivered 5 µl/hr for 14 days. Pumps were implanted subcutaneously at the time of cell transfer. Rats received 350 mg/kg/day of castanospermine.

b. Results

Hind feet of rats were measured in 4 diameters beginning the day of cell transfer. The measurements are averaged and expressed as % change in volume of feet.

Two experiments have been performed both treating rats with 350 mg/kg/day castanospermine beginning the day of cell transfer. The results are shown in Table 5.

TABLE 5

Effect of CS on passively induced adjuvant arthritis.

| Exp. 1 $50 \times 10^6$ cells | % Δ in foot volume | |
|---|---|---|
| Control | Day 7 | Day 14 |
| 1 | +18% | +40% |
| 2 | +22% | +26% |
| 3 | +17% | +32% |
| 4 | +18% | +25% |
| 5 | +16% | +25% |
| CS treated $50 \times 10^6$ cells | | |
| 1 | +12% | +4% |
| 2 | +5% | −1% |
| 3 | 5% | 0 |
| 4 | 0 | +9% |
| Exp. 2 $0 \times 10^6$ cells | % Δ in foot volume | |
| 1 | +12% | +40% |
| 2 | +31% | +99% |
| 3 | +17% | +77% |
| 4 | +21% | +18% |
| 5 | +28% | +45% |

TABLE 5-continued

Effect of CS on passively induced adjuvant arthritis.

| Exp. 1 50 × 10⁶ cells | % Δ in foot volume | |
| --- | --- | --- |
| Control | Day 7 | Day 14 |
| CS treated 60 × 10⁶ cells | | |
| 1 | −5% | −8% |
| 2 | −7% | −18% |
| 3 | −3% | −14% |
| 4 | +3% | −1% |

In no case did any of the CS treated rats show inflammation and only one (#1, Exp 1) showed moderate swelling at a single time period. All rats in experiment 1 were killed for histological examination.

In experiment 2 the osmotic pumps were removed on day 15 and all animals followed out to day 28+. Controls continued to show very significant degrees of swelling and inflammation whereas CS treated rats remained normal; even 2 weeks after drug was discontinued.

EXAMPLE 4

Example 3 demonstrates the effect of parenterally administered CS on passively induced adjuvant arthritis. Other experiments have shown that CS is effective in preventing passively transferred adjuvant arthritis when the drug is administered orally in the drinking water beginning three days before cell transfer; the results of a typical experiment are shown in Table 6. Even when disease symptoms occurred in the treated animals they were less severe, both histologically and morphologically. It was not possible to treat animals with higher doses of CS by this route since they refused to consume water containing higher concentrations of drug.

TABLE 6

Effect of orally administered CS on passively induced adjuvant arthritis.

| | % Δ in foot volume | |
| --- | --- | --- |
| Control | Day 7 | Day 14 |
| 1 | 1 | 64 |
| 2 | 20 | 108 |
| 3 | 3 | 40 |
| 4 | 9 | 108 |
| 5 | 12 | 102 |
| 6 | 15 | 82 |
| CS treated[a] | | |
| 1 | 1 | 44 |
| 2 | −1 | 7 |
| 3 | −1 | 9 |
| 4 | 2 | 36 |
| 5 | −3 | 12 |
| 6 | 3 | 26 |

[a]CS was delivered in drinking water (1.35 g/litre) beginning 3 days before cell transfer; animals consumed an average of 83 mg/kg/day.

EXAMPLE 5

Effect of Castanospermine on Passively Induced Adjuvant Arthritis

In separate experiments to determine the effect of CS on passively induced adjuvant arthritis, the methods of Example 3 were repeated, however the treatment with CS (325 mg/kg/day) was commenced 7 days after injection of cells (60×10⁶ cells/rat).

Figure 5:
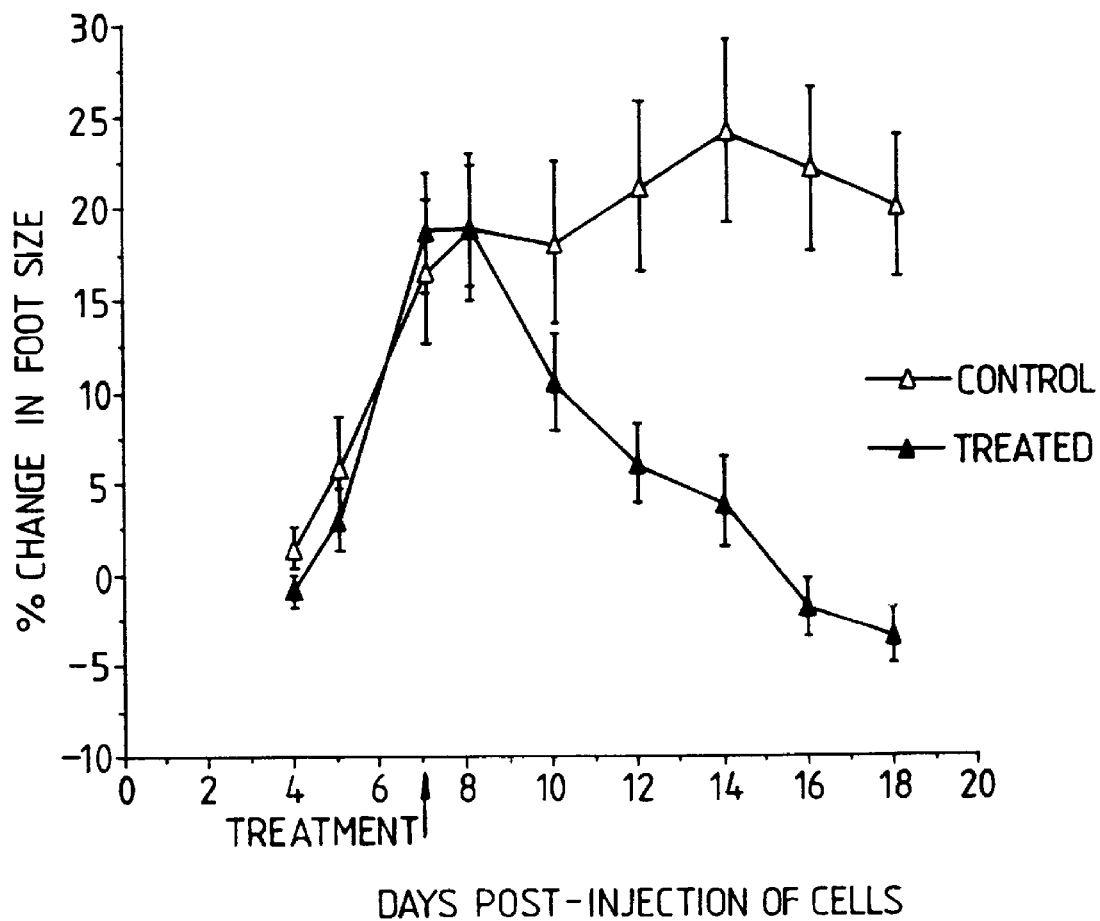
FIGS. 5 and 6 are graphs which show percent change in foot size of treated and control rats.
Figure 6:
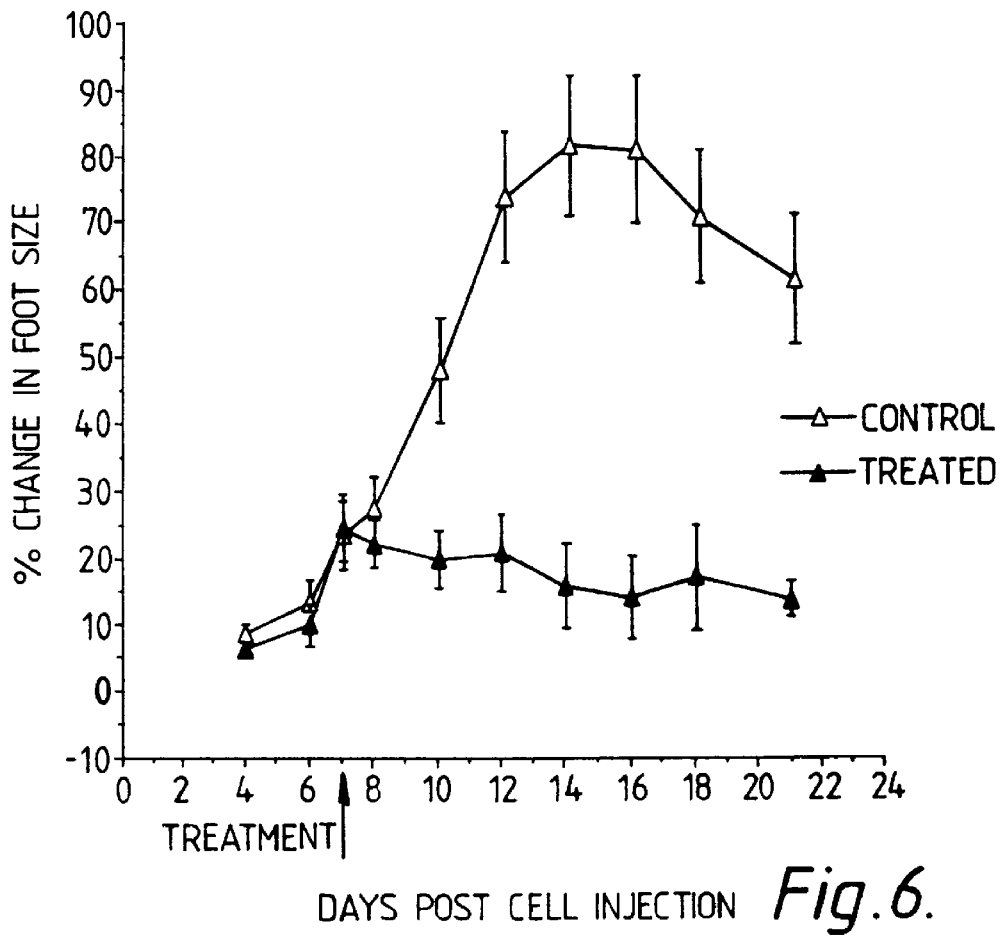

The results of two separate experiments showing % change in foot size of treated and control rats (5 rats/group) are shown graphically in FIGS. 5 and 6.

EXAMPLE 6

Example 5 also demonstrates the effect of parenterally administered CS on passively induced adjuvant arthritis. Other experiments have shown that CS will, to a large degree, block the progression of passively transferred adjuvant arthritis when treatment is initiated after the disease is established. Table 7 shows that when CS is administered in the drinking water to animals with established arthritis on day 7 following cell transfer, progression of the disease is slowed dramatically or in some cases halted altogether.

TABLE 7

Effect of orally administered cs on established passively induced adjuvant arthritis.

| | % Δ in foot volume | |
| --- | --- | --- |
| Control | Day 7 | Day 14 |
| 1 | 30 | 109 |
| 2 | 44 | 102 |
| 3 | 39 | 121 |
| 4 | 30 | 90 |
| 5 | 60 | 142 |
| mean | 41 | 113 |
| CS treated[a] | | |
| 1 | 29 | 40 |
| 2 | 33 | 92 |
| 3 | 34 | 46 |
| 4 | 30 | 86 |
| 5 | 32 | 27 |
| 6 | 38 | 41 |
| mean | 33 | 60 |

[a]CS was delivered in drinking water (1.35 g/litre) beginning 7 days after cell transfer; animals consumed an average of 80 mg/kg/day.

EXAMPLE 7

Effect of Castanospermine on Actively Induced Arthritis

Figure 7:
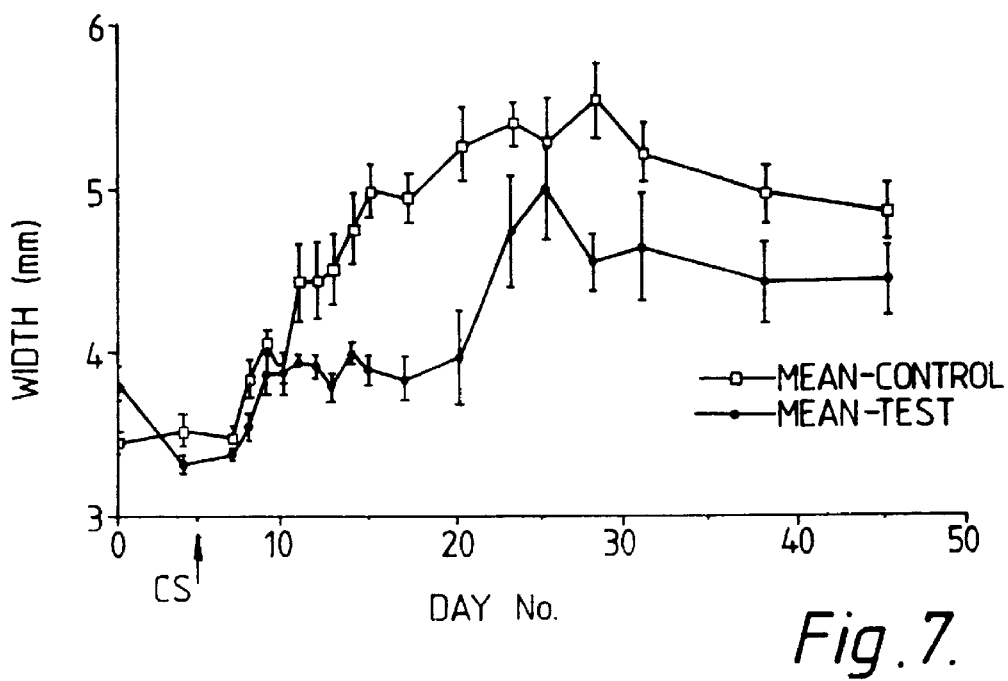
FIGS. 7, 8, and 9 are graphs which show the change in mid foot widths, mean mid foot circumferences and mean ankle widths respectively for control and test groups of rats for a period of 50 days.
Figure 8:
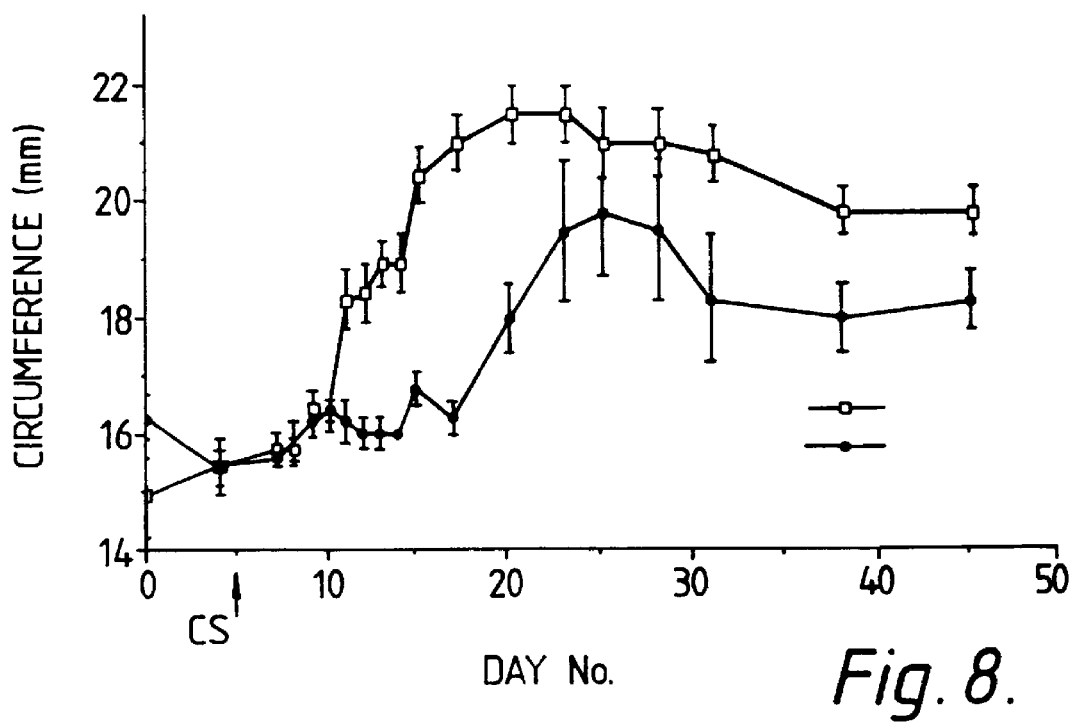
Figure 9:
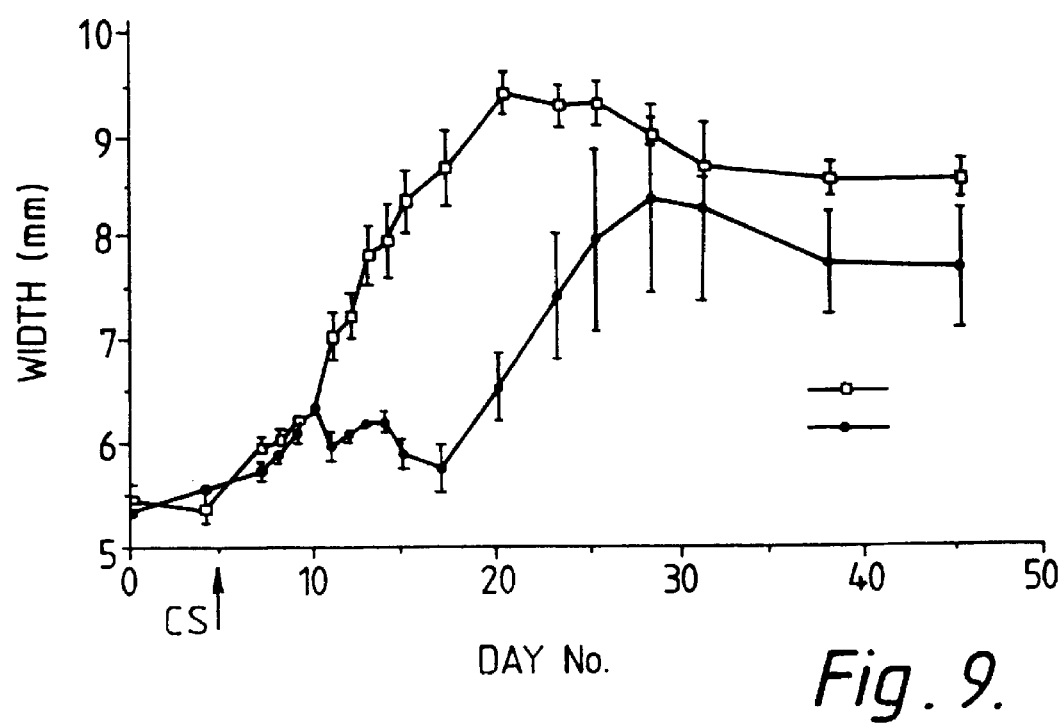

In this example, arthritis was actively induced in rats by the injection of *M. butyricum* in light mineral oil at the base of the tail and at several subcutaneous sites over the lower back. Mid foot and ankle widths were measured over a period of 50 days. Arthritic changes were noticeable after 10 days. Pumps delivering 200 mg/kg/day castanospermine were implanted at day 5 after injection of *M. butyricum*. 7 rats were used in both test and control groups. The results in the control and test groups are shown graphically in FIGS. 7, 8 and 9, comparing mid foot widths, mean mid foot circumferences and mean ankle widths, respectively.

EXAMPLE 8

Immunosuppressive Effect of Castanospermine in Transplantation of Pancreatic Islets a. Methods Donor mice were BALB/c (H2$^d$) and recipients were CBA (H2$^k$). Donor pancreatic islets were prepared using standard techniques. Approximately 400 islets were isolated from 10 donor mice. These freshly isolated islets, in groups of 50, were placed into CBA blood clots and these were placed under the kidney capsule of CBA mice which were diabetic (blood glucose 20 mM/liter).

Two recipients were implanted (subcutaneously) with miniosmotic pumps containing CS at the time of islet transplantation. These pumps delivered CS at a dose of 300 mg/kg/mouse/day for a period of 14 days. Two control mice were sham operated.

Blood samples (10 ml) were taken daily and assayed for blood glucose using an automatic analyser (Beckman Glucose Analyzer 2).

b. Results

All transplant recipients became normoglycaemic within 24 hours indicating successful transplantation of all of the grafts. Rejection of grafts was assumed to occur when animals became hyperglycaemic. Control animals rejected on days 9 and 12.

One CS treated mouse did not reject until day 19, five days after the miniosmotic ceased to function. The other CS treated animal rejected on day 12. The reason for this became apparent when the miniosmotic pump was removed and examined and found not to have delivered its CS payload.

EXAMPLE 9

Effect of Castanospermine in Renal Graft Survival

This example demonstrates graft survival of DA rats receiving renal allografts from fully allogeneic (DA/LEW) donors treated with castanospermine. One kidney from each rat was replaced with a donor kidney, after which the remaining original rat kidney was removed. The results are set out in Table 8 below:

TABLE 8

| Number of Rats | Concentration of Castanospermine | No. of rats surviving ≧ 14 days | Mean No. of days of Survival |
| --- | --- | --- | --- |
| 8 | 100 mg/kg | 5 | 36.5 |
| 8 | no pump | 0 | — |
| **6 DA/DA | no pump | 6 | 100 |

*This control has been performed on many other occasions and no rat has ever survived more than 14 days.
**Syngenetic control.

EXAMPLE 10

Delayed Hypersensitivity (DTH): Effect of Castanospermine

C57BL mice were given $10^8$ sheep red blood cells (SRBC) intravenously. Five days later $10^5$ SRBC in a volume of 10 μl was injected into the left hind footpad and 10 μl saline into the right. Castanospermine was given every 4 hours i.p. beginning at the time of footpad testing. Total dose of CS over 24 hrs was 300 mg/kg/mouse. Control mice were given saline every 4 hours, and 5 mice/group were used in both test and control groups.

In the control group, a 33% increase in foot swelling resulted, whereas the corresponding increase in foot swelling in the test group receiving CS was 11%.

EXAMPLE 11

Figure 10:
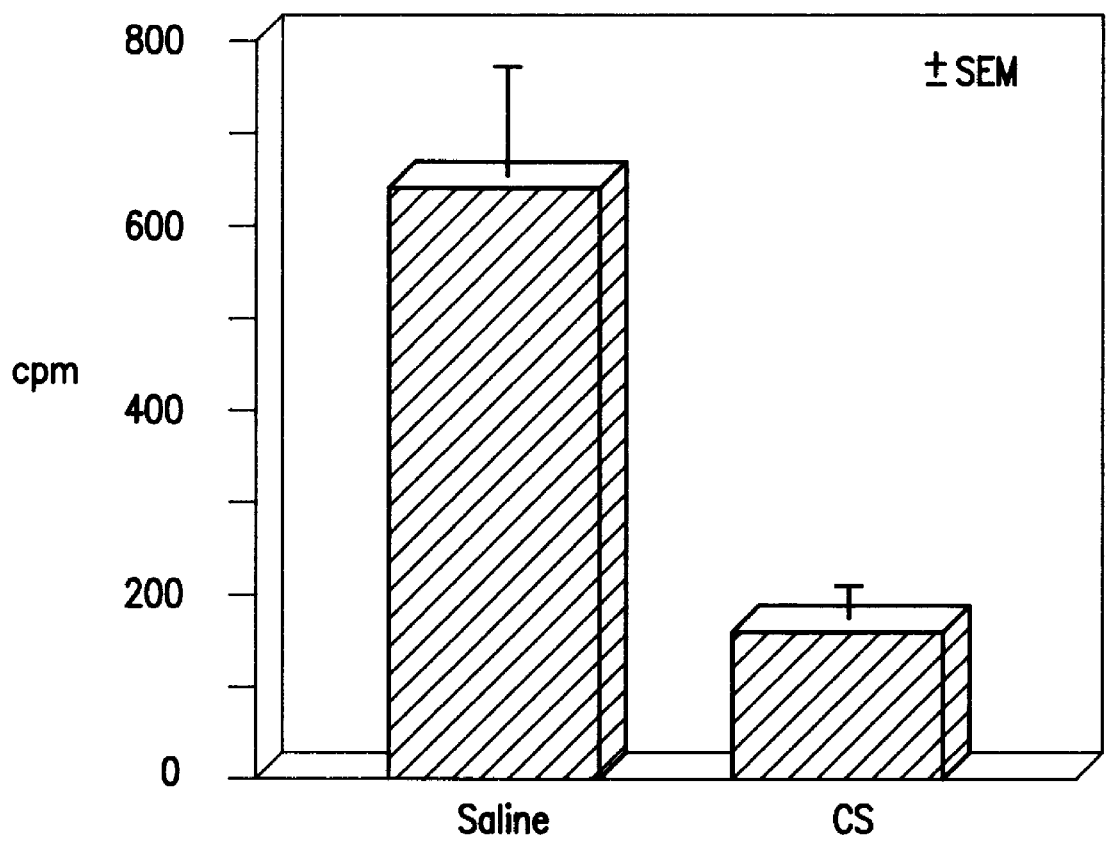
FIG. 10 is a graph which shows the ability of castonospermine to block the generation of effector cells in a contact sensitivity model.

A further demonstration of the immunosuppressive activity of CS lies in its ability to block the generation of effector cells in a contact sensitivity model. In this example CBA mice were sensitized with picryl chloride then injected intraperitoneally with castanospermine at 150 mg/kg or saline twice a day for 7 days beginning on the day of sensitization. Their spleen cells were then isolated and labelled with $^{51}$Cr and injected into naive recipients. The recipient animals were challenged with picryl chloride on one ear and vehicle on the other and 7 hours later counts were taken on the control and treated ears. As shown in FIG. 10, cells from animals treated with castanospermine during the sensitization period were ineffective at transferring contact sensitivity. The values shown are mean values of counts per minute in the picryl chloride treated ears minus counts per minute in the vehicle treated ears±SEM. This inhibition of generation of effector cells in contact sensitivity is additional evidence of the immunosuppressive activity of castanospermine to that seen in the organ allograft studies in rats.

EXAMPLE 12

It has been found that proliferation of antigen-specific T cell lines is inhibited, in a dose-dependent manner, by CS. As shown in Table 9, when myelin basic protein (MBP) specific T cell lines were stimulated with irradiated syngenetic thymocytes plus MBP in the presence or absence of various concentrations of castanospermine it was found that CS inhibited T cell proliferation in a dose dependent manner as measured by tritiated thymidine incorporation.

TABLE 9

Suppression of proliferation of neuroantigen specific T cell lines by castanospermine.

| Treatment | cpm$^a$ × $10^3$ |
| --- | --- |
| no MBP | 0.5 |
| MBP | 162 |
| MBP + 1 μg/ml CS | 120 |
| MBP + 10 μg/ml CS | 110 |
| MBP + 50 μg/ml CS | 26 |
| MBP + 100 μg/ml CS | 24 |

$^a$Tritiated thymidine incorporation. CS was added at time 0 and the counts were determined 72 hours later.

REFERENCES

1. Bernard, C. C. A., P. R. Carnegie and I. R. Mackay (1983), Immunoregulatory mechanisms in experimental autoimmune encephalomyelitis and multiple sclerosis. In: J. F. Hallpike, C. W. Adams and W. W. Tourellotte (Eds.) "Multiple Sclerosis", Chapmen and Hall, London, pp.479–511.
2. Chambers, J. P. and A. D. Elbein (1986), Effects of castanospermine on purified lysosomal alpha-1,4-glucosidase. Enzyme, 35:53–56.
3. Deibler, G. E., R. E. Martenson and M. W. Kies (1972), Large scale preparation of myelin basic protein from central nervous tissue of several mammalian species. Prep. Biochem. 2:139–165.
4. Ellmers, B. R., B. L. Rhinehart and K. M. Robinson (1987). Castanospermine: an apparent tight-binding inhibitor of hepatic lysosomal alpha-glucosidase. Biochem. Pharmacol. 36:2381–2385.
5. Figura, K. von and A. Hasilik (1986). Lysosomal enzymes and their receptors. Ann. Rev. Biochem. 55:167–193.
6. Gross, V., T.-A. Tran-Thi, R. T. Schwarz, A. D. Elbein, K. Decker and P. C. Heinrich (1986). Different effects of the glucosidase inhibitors 1-deoxynojirimycin, N-methyl-1-deoxynojirimycin and castanospermine on the glycosylation of rat $a_1$-acid glycoprotein. Biochem. J. 236:853–860.

7. Hinrichs, D. J., C. M. Roberts and F. J. Waxman (1981). Regulation of paralytic experimental allergic encephalomyelitis in rats: susceptibility to active and passive disease reinduction. *J.Immunol.* 126:1857–1862.
8. Hohenschultz, L. D., E. A. Bell, P. J. Jewess, D. P. Leworthy, R. J. Pryce, E. Arnold and J. Clardy (1981). Castanospermine, a 1,6,7,8-tetrahydroxy-octahydroindolizine alkaloid, from the seeds of *Castanospermum australe*. *Phytochemistry* 20:811–814.
9. Humphries, M. J., K. Matsumoto, S. L. White and K. Olden (1986).
Inhibition of experimental metastasis by castanospermine in mice blockage of two distinct stages of tumor colonization by oligosaccharide processing inhibitors. *Cancer Res.* 46:5215–5222.
10. Kornfield, S. (1987). Trafficking of lysosomal enzymes. *FASEB Journal* 1:462–468.
11. Levine, S. and R. Sowinski 91968). Passive transfer of allergic adrenalitis and encephalomyelitis with whole blood.
Proc.Soc.Exp.Biol.Med. 129:221–223.
12. Panitch, H. S. and D. E. McFarlin (1977). Experimental allergic encephalomyelitis: enhancement of cell-mediated transfer by concanavalin A. *J.Immunol.* 119:1134–1137.
13. Paterson, P. Y. (1960). Transfer of allergic encephalomyelitis in rats by means of lymph node cells. *J.Exp.Med.* 111:119–136.
14. Paterson, P. Y. (1976). Experimental autoimmune (allergic) encephalomyelitis. In: P. A. Miescher and H. J. Muller-Eberhand (Eds.) "Textbook of Immunopathology", Grune and Stratton, New York, pp.179–213.
15. Sasak, V. W., J. M. Ordovas, A. D. Elbein and R. W. Berninger (1985). Castanospermine inhibits flucosidase I and glycoprotein secretion in human hepatoma cells. *Biochem. J.* 232:759–766.
16. Saul, R., J. P. Chambers, R. J. Molyneaux and A. D. Elbein (1983).
Castanospermine, a tetrahydroxylated alkaloid that inhibits β-glucosidase and β-glucocerebrosidase. *Arch. Biochem. Biophys.* 221:593–597.
17. Saul, R., J. J. Ghidoni, R. J. Molyneaux and A. D. Elbein (1985). Castanospermine inhibits α-glucosidase activities and alters glycogen distribution in animals. *Proc. Natl. Acad. Sci.* (USA). 82:93–97.
18. Stone, S. H. (1961). Transfer of allergic encephalomyelitis in rats by means of lymph node cells in inbred guinea pigs. *Science* 134:619–620.
19. West, C. M. (1986). Current ideas on the significance of protein glycosylation. *Mol. Cell.Biochem.* 72:3–20.
20. Willenborg, D. O. (1979). Experimental encephalomyelitis in the Lewis rat: studies on the mechanism of recovery from disease and acquired resistance to reinduction. *J.Immunol.* 123: 1145–1150.
21. Willenborg, D. O. and C. R. Parish (1988). Inhibition of allergic encephalomyelitis in rats by sulfated polysaccharides. *J.Immunol.* 140:3401.

We claim:

1. A method of anti-inflammatory treatment of a warm-blooded animal patient in need of said treatment, which comprises administration to the patient of an anti-inflammatory-effective amount of castanospermine.

2. A method according to claim 1, wherein said patient is a human.

3. A method according to claim 1, wherein said effective amount of castanospermine comprises from 10 to 500 mg/kg/day.

4. A method according to claim 1, wherein the castanospermine is orally administered.

5. A method according to claim 1, wherein said castanospermine is administered to a patient in need of anti-inflammatory treatment prior to onset of clinical symptoms requiring anti-inflammatory treatment.

6. A method according to claim 5, wherein the castanospermine is administered parenterally.

7. A method according to claim 6, wherein the parenteral administration is by injection.

8. A method according to claim 5, wherein the castanospermine is orally administered.

9. A method according to claim 1, wherein said treatment comprises treatment of arthritis.

10. A method according to claim 9, wherein the castanospermine is administered parenterally.

11. A method according to claim 10, wherein the parenteral administration is by injection.

12. A method according to claim 9, wherein the castanospermine is orally administered.

13. A method according to claim 1, wherein the castanospermine is administered parenterally.

14. A method according to claim 13, wherein the parenteral administration is by injection.

\* \* \* \* \*